United States Patent
Suzuki et al.

(10) Patent No.: US 8,547,546 B2
(45) Date of Patent: Oct. 1, 2013

(54) SURFACE-DEFECT INSPECTION DEVICE

(75) Inventors: Katsuya Suzuki, Hitachinaka (JP); Takahiro Jingu, Takasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/390,342

(22) PCT Filed: Sep. 14, 2010

(86) PCT No.: PCT/JP2010/065781
§ 371 (c)(1),
(2), (4) Date: Feb. 14, 2012

(87) PCT Pub. No.: WO2011/040223
PCT Pub. Date: Apr. 7, 2011

(65) Prior Publication Data
US 2012/0147363 A1    Jun. 14, 2012

(30) Foreign Application Priority Data
Sep. 30, 2009    (JP) .................................. 2009-227873

(51) Int. Cl.
*G01N 21/00*    (2006.01)
(52) U.S. Cl.
USPC .................................................... 356/237.4
(58) Field of Classification Search
None
See application file for complete search history.

(56) References Cited

U.S. PATENT DOCUMENTS 7,426,031 B2 *   9/2008   Kim et al. ..................... 356/392
7,675,613 B2     3/2010   Nakao et al.

FOREIGN PATENT DOCUMENTS

| JP | 8-219943    | 8/1996  |
|----|-------------|---------|
| JP | 2004-295879 | 10/2004 |
| JP | 2006-145269 | 6/2006  |
| JP | 2009-180691 | 8/2009  |

OTHER PUBLICATIONS

Office Action in JP 2009-227873, mailed Dec. 4, 2012, (in Japanese, 1 pg.) [including English language translation, 1 pg.].

* cited by examiner

*Primary Examiner* — Gregory J Toatley
*Assistant Examiner* — Amanda Merlino
(74) *Attorney, Agent, or Firm* — Antonelli, Terry, Stout & Kraus, LLP.

(57) ABSTRACT

A data processing and controlling portion calculates the amounts of coordinate deviations between the artificial defects on the standard sample and the detected defects, checks the sensitivity (instrumental sensitivity (luminance, brightness, or the like)), and proceeds to execution of hardware corrections. If the coordinate deviation is less than a certain value, software corrections are carried out. In the case of the software corrections, coordinate corrections are made for the whole standard sample. The amounts of coordinate deviations are computed and checked. If the amounts of coordinate deviations are outside a tolerance, coordinate corrections are made for each region obtained by dividing the standard sample.

10 Claims, 9 Drawing Sheets

SURFACE-DEFECT INSPECTION DEVICE

TECHNICAL FIELD

The present invention relates to an optical surface-defect inspection device and surface-defect inspection method for inspecting foreign matter, defects, or the like on a surface of an inspected object during manufacturing steps for semiconductor devices or the like.

BACKGROUND ART

The accuracy of the coordinates of each defect detected by optical defect inspection device is important performance, for example, in identifying defective parts on a semiconductor device, observing the defects with a review device, classifying the defects, and making a decision as to whether each defect is good or not. In recent years, as semiconductor devices have been manufactured with ever decreasing sizes, the requirements for defect coordinate accuracy have become more stringent year by year.

In the conventional optical defect inspection device, actual foreign matter has been used in identifying or correcting the positions of defects and making corrections to the coordinates at which defects are detected for observations with a defect review device. In the conventional coordinate correction method, the amount of deviation in the direction of rotation, the amount of elongating or contracting deviation, the amount of deviation of conveyance, and the amount of deviation of an optical axis are calculated, and a correction is made using the whole object to be inspected.

With the conventional technique of review devices, it is customary that coordinate corrections are made for defects of somewhat large size by the use of known defects and then fine corrections are made for defects of smaller sizes and that the coordinates of the review device are corrected.

As described in patent literatures, it is usual that defect sizes and positions are forecasted based on the results of detection of defects made by a defect inspection device and a correction is made on the side of the review device such that defects can be quickly brought to within the screen and captured.

Furthermore, based on the position of a defect on an inspected object observed with a review device, the same inspected object is inspected by a defect inspection device, the coordinates are corrected from the results of the inspection, and then a different sample is inspected.

Based on the results of an inspection of a different sample made by the defect inspection device, defects are observed with the review device. In practice, however, coordinate corrections are again made in conformity with actual defects by the review device.

CITATION LIST

Patent Literatures

Patent literature 1: JP-A-2006-145269

SUMMARY OF INVENTION

Technical Problem

In an optical defect inspection device, there is a demand for improvement of the defect coordinate accuracy. There exists the problem that with the total coordinate correction of the inspected object, errors in individual regions (due to undulation of the sample or the like) cannot be fully corrected.

It is an object of the present invention to realize surface-defect inspection device and surface-defect inspection method capable of improving the accuracy of the coordinates of defects and reducing errors in the coordinates of detected defects.

Solution to Problem

In order to achieve the above-described object, the present invention is configured as follows.

In surface-defect inspection device and surface-defect inspection method, a standard sample on which defects of known coordinates have been previously formed is illuminated with illuminating light. Scattering light from the standard sample is detected, and the image coordinates of the defects on the surface are corrected. Based on the corrected image coordinates, defects on the surface of the inspected object are inspected.

Advantageous Effects of Invention

Surface-defect inspection device and surface-defect inspection method capable of improving the accuracy of the coordinates of defects and reducing errors in the coordinates of the detected defects can be accomplished.

Other objects, features, and advantages of the present invention will be apparent from the following description of the embodiments of the present invention provided in connection with the accompanying drawings.

DESCRIPTION OF EMBODIMENTS

Embodiments of the present invention are hereinafter described with reference to the accompanying drawings.

Embodiment 1

Figure 1:
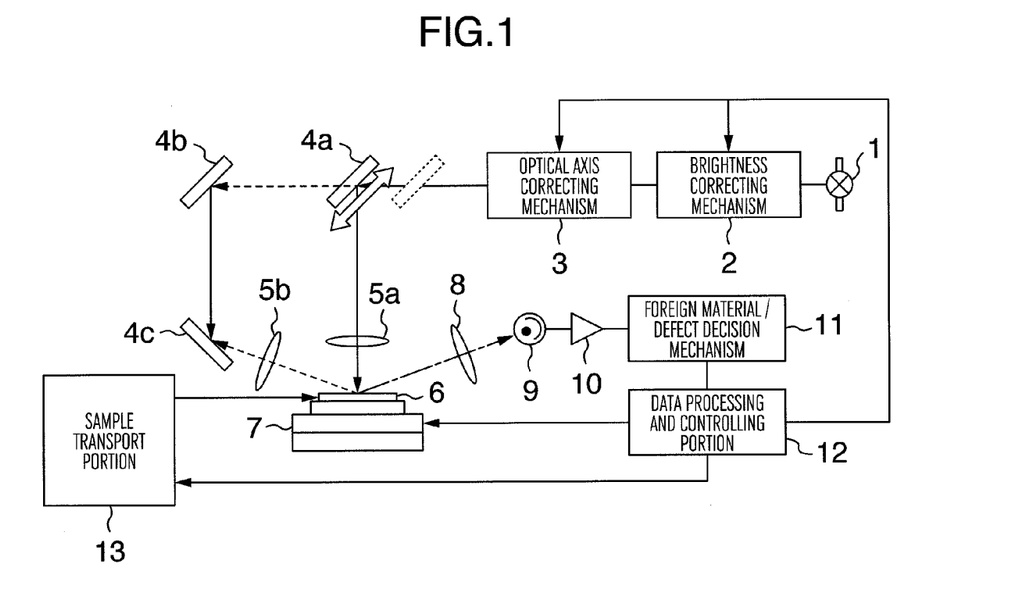
FIG. 1 is a schematic block diagram of an optical defect inspection device to which the present invention is applied.

FIG. 1 is a schematic block diagram of an optical surface-defect inspection device that is embodiment 1 of the present invention.

In FIG. 1, light emitted from a light source 1 passes through a light amount adjusting mechanism 2 capable of adjusting the brightness and through an optical axis correcting mechanism 3 and is made to hit an inspected object 6 via a mirror 4a and a condenser lens 5a. The light emitted from the light source 1 also passes through the light amount adjusting mechanism 2 and the light axis correcting mechanism 3 and is made to hit the inspected object 6 via the mirror 4a, a mirror 4b, a mirror 4c, and a condenser lens 5b.

The inspected object 6 is disposed on an XZ seater stage 7 having a rotary stage, a straight motion X stage, and a heightwise direction Z stage. Scales permitting one to know positional coordinates are disposed on the stages, respectively.

Furthermore, the defect inspection device has a foreign material/defect decision mechanism 11 for recording the coordinates of positions at which scattering light from defects on the inspected object 6 is detected from the scales of the stage 7 and for computing the coordinates of the defects, as well as a data processing and controlling portion 12 for correcting the positions of the defects. In addition, the defect inspection device is equipped with a sample transport portion 13 for moving the stage 7 in accordance with an instruction signal from the data processing and controlling portion 12.

Light scattered from the inspected object 6 is sent to the foreign material/defect decision mechanism 11 via a lens 8, a detector 9, and an amplifier 10.

The data processing and controlling portion 12 analyzes the positions, sizes, and shapes of defects on the inspected object 6 from the aforementioned stage position and from scattering light data.

The data processing and controlling portion 12 corrects the detected coordinates and provides feedback control of the mechanisms, i.e. stage 7, brightness correcting mechanism 2, and light axis correcting mechanism 3, to thereby control their operations and provide an output indicative of ultimate defect information about the inspected object 6.

Figure 2:
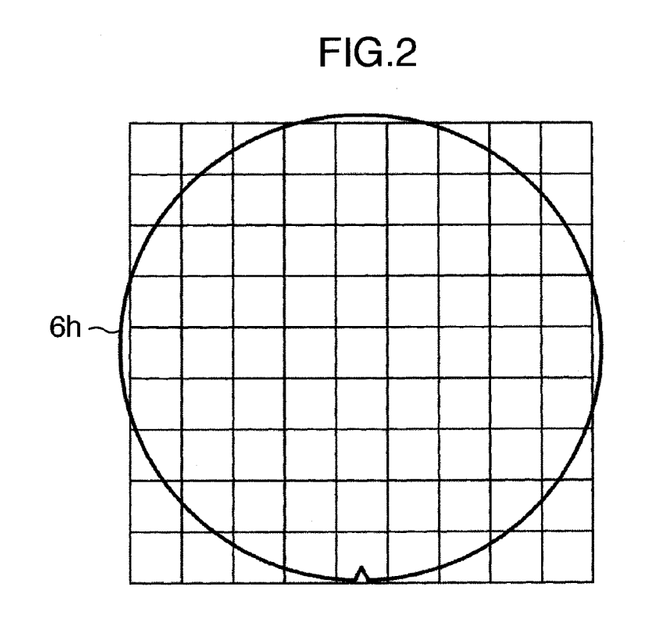
FIG. 2 is a view showing an example of how a standard sample is divided into regions in embodiment 1 of the invention.

FIG. 2 is a view showing an example of how a standard sample 6h is divided into regions in embodiment 1 of the invention. Although the size and shape of each region obtained by the division can be specified at will, the data processing time is preferably set to a bare minimum because the time depends on the number of the regions and on their shape.

The example shown in FIG. 2 is an example of a case where the shape of each region obtained by a division is a square.

Figure 3:
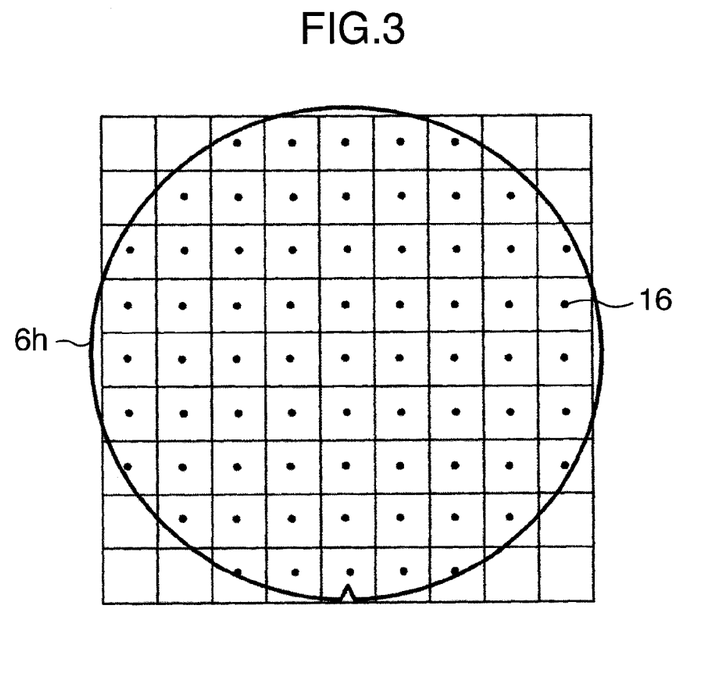
FIG. 3 is an explanatory view of artificial defects on a standard sample in embodiment 1 of the invention.

FIG. 3 is a view showing an example in which defects are formed on the standard sample 6h in embodiment 1 of the present invention. In the example of FIG. 3, artificial defects 16 are disposed at known positions which are spaced at equal intervals like a grid (i.e., defects of previously known coordinates are formed). The shape, size, and positions of the defects are so set that they can be detected using scattering light.

Note that at least one defect is formed in each region of the grid-like area.

Preferably, the size and shape of each artificial defect 16 are set at will according to the purpose of use. The artificial defects 16 are formed by a focused ion beam (FIB) instrument.

Figure 4:
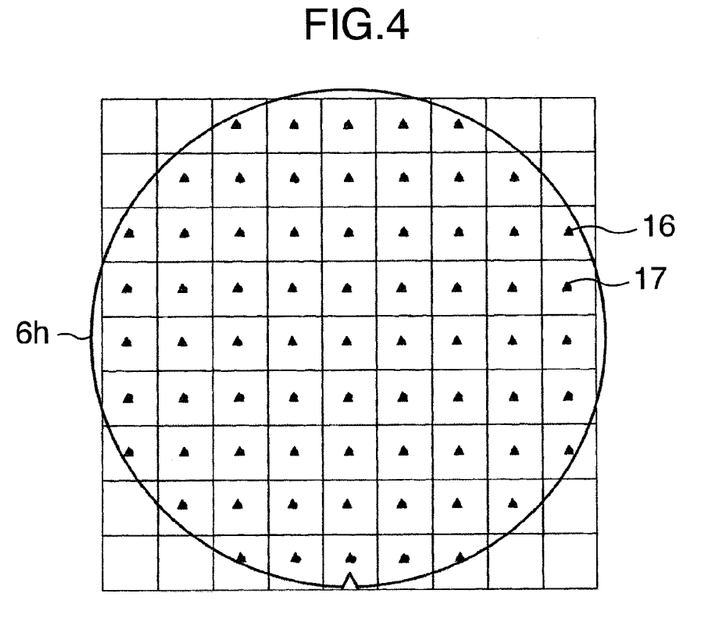
FIG. 4 is an explanatory view of the difference between the artificial defects on the standard sample in embodiment 1 of the invention and an image of detected defects.

FIG. 4 is a view showing the results of an inspection of the artificial defects machined or processed in the standard sample 6h in embodiment 1 of the invention. In FIG. 4, the artificial defects 16 and detected defects 17 are simultaneously shown.

Figure 5:
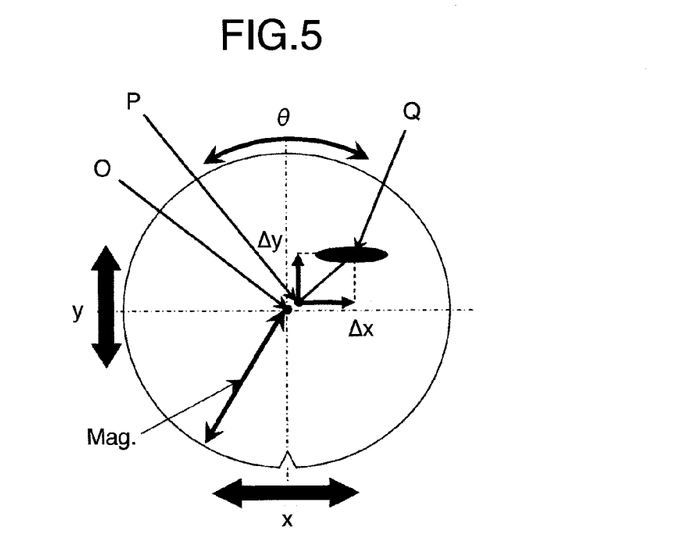
FIG. 5 is an explanatory view of information that is discernible from the image of detected defects in embodiment 1 of the invention.

FIG. 5 is a diagram illustrating positional deviation information that is found from the results of an inspection of the standard sample 6h in embodiment 1 of the present invention. In FIG. 5, the O indicates the center of the object to be inspected. The P indicates the center of the rotary stage. The Q indicates the position of the center of the beam. The $\Delta x$ and $\Delta y$ are amounts of deviation of the beam position. The $\Delta x$ indicates the deviation between the center of the rotary stage and the position of the beam center, taken in the X-direction. The $\Delta y$ indicates the deviation between the center of the rotary stage and the central position of the beam, taken in the Y-direction. The $\theta$, x, and y are the amounts of deviation of the position into which the wafer is carried. The $\theta$ indicates the amount of deviation in the rotational direction. The offset x indicates the amount of deviation of conveyance in the X-direction (wafer shift in the X-direction). The offset y indicates the amount of deviation of conveyance in the Y-direction (wafer shift in the Y-direction). The Mag. is an amount of elongating or shrinking deviation and indicates the magnification error (error in the stage scale) in the R-direction.

In FIG. 5, the amount of deviation in the rotational direction, the amount of elongating or shrinking deviation (magnification), the amounts of offset deviations (conveyance errors), and the amounts of deviation of the optical axis that are parameters are obtained from the results of the inspection. That is, parameter information is obtained. For example, by correcting the parameters, information about the detection position obtained from the inspected object 6 by the review device is used as reference data. The results of an inspection obtained by a defect inspection device are matched with the reference data, and the detection position can be corrected.

Figure 6:
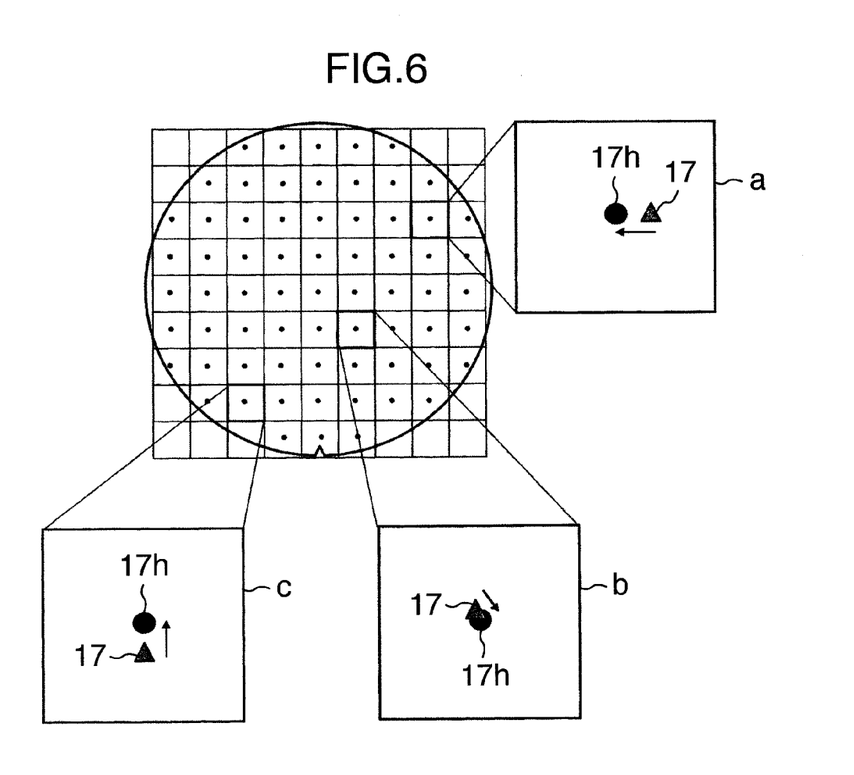
FIG. 6 is an explanatory view of a case in which a fine adjustment is made after a rough adjustment in embodiment 1 of the invention.

FIG. 6 is a view illustrating a method consisting of making rough adjustments using the parameters (all the coordinates are corrected (e.g., all the coordinates are corrected by moving them in the X-(-Y)-axis direction)), then dividing the inspected object 6 like a grid into regions, and making fine adjustments of positional coordinates in each region (a positional adjustment is made independent of other regions). Errors that cannot be fully corrected with rough adjustments (such as waviness of the sample) can be corrected with these fine adjustments. Consequently, errors can be reduced.

For example, where the detection position after a rough correction is as shown in FIG. 6, a defect 17 existing in a region a is finely corrected to a position 17h in the direction of the arrow. Similarly, in regions b and c, fine corrections are made in the directions of the arrows. The positions of defects can be detected more accurately by making a fine correction in each region over the whole surface of the inspected object 6.

Figure 7:
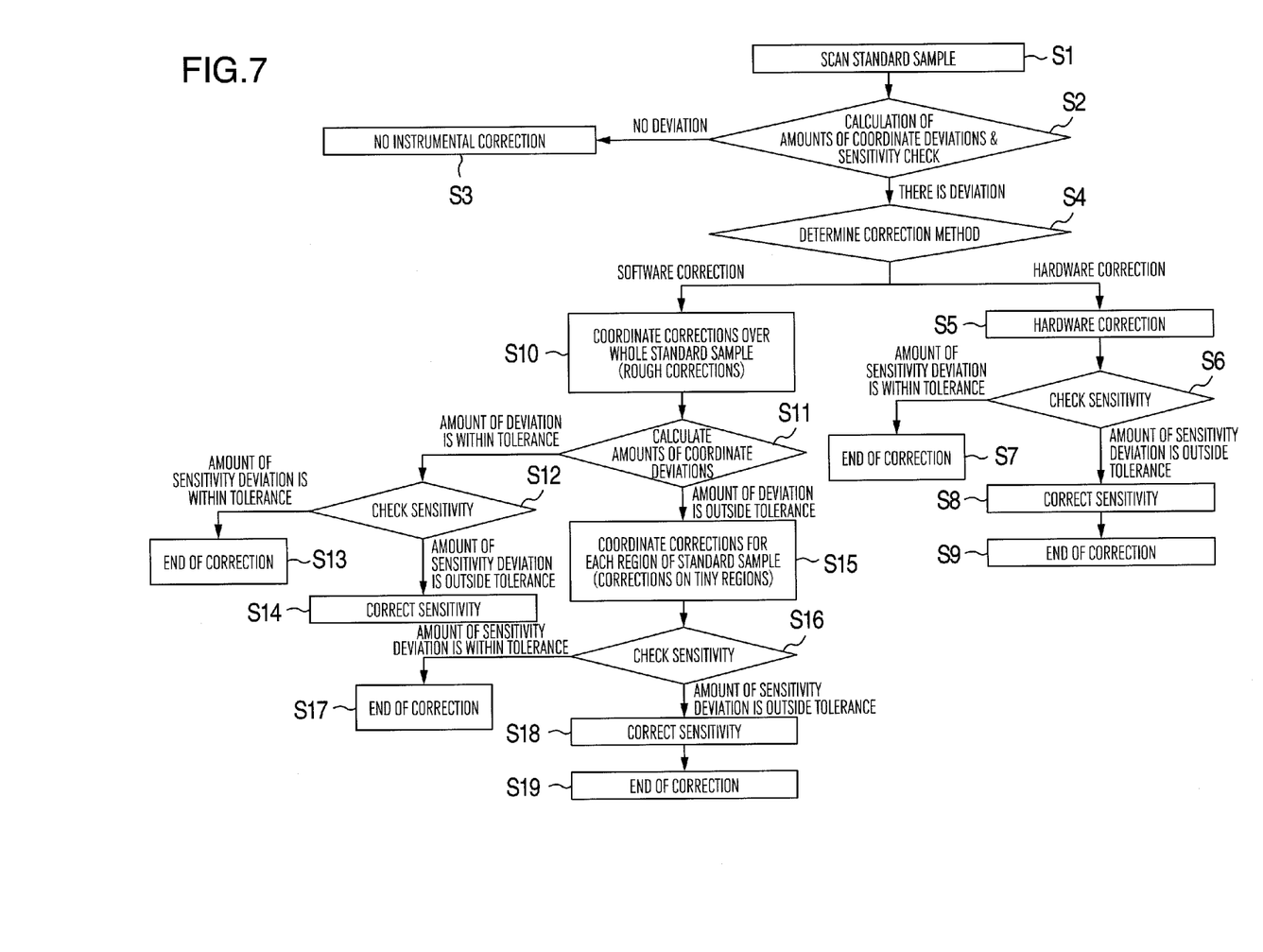
FIG. 7 is a flowchart of operations in embodiment 1 of the invention.
Figure 8:
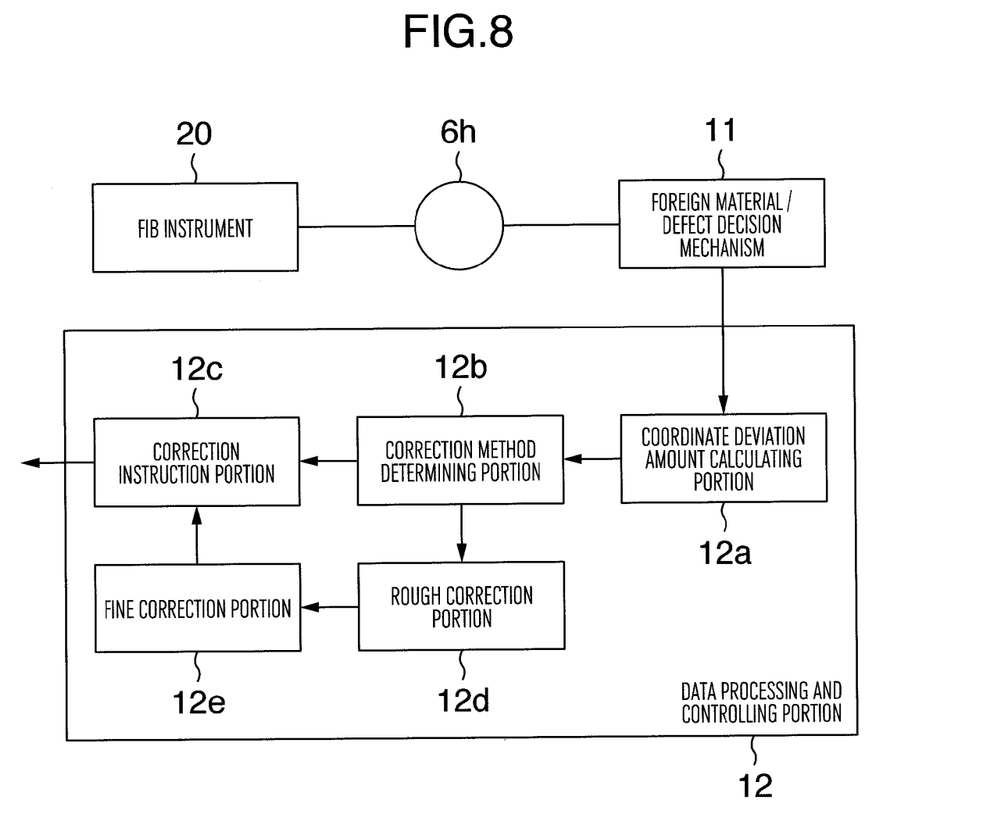
FIG. 8 is a functional block diagram of a data processing and controlling portion in embodiment 1 of the invention.

FIG. 7 is a flowchart of operations for position corrections made by the defect inspection device in embodiment 1 of the present invention. FIG. 8 is a functional block diagram of a data processing and controlling portion that carries out the flow of operations illustrated in FIG. 7.

In step S1 of FIG. 7, artificial defects are formed on the standard sample 6h by FIB 20. A decision is made regarding defects by the foreign material/defect decision mechanism 11. Defect data is supplied to a coordinate deviation amount calculating portion 12a of the data processing and controlling portion 12.

In step S2, the coordinate deviation amount calculating portion 12a calculates the amount of coordinate deviations between each artificial defect 16 on the standard sample 6h and the detected defect 17 and checks the sensitivity (instrumental sensitivity (luminance, brightness, or the like)). If there is no deviation in the coordinate position or if the coordinate position deviation is within a given range, no instrumental correction is made (step S3).

In a case where the deviation of the coordinate position is more than the given value in step S2, a correction method determining portion 12b determines a method of correction (step S4). If the coordinate deviation is in excess of a certain value in step S4, control goes to execution of the hardware correction (mechanical or optical adjustment of a mechanism for detecting scattering light). If the coordinate deviation is less than the certain value, a software correction is carried out.

If the decision at step S4 is that a hardware correction is needed, control goes to step S5, where a correction instruction portion 12c supplies correction instruction signals to the brightness correcting mechanism 2, the optical axis correcting mechanism 3, and so on. Control then goes to step S6, where the correction instruction portion 12c checks the aforementioned sensitivity. If it is within an allowable value, the correction is ended (step S7).

If the amount of sensitivity deviation is in excess of the allowable value in step S6, control proceeds to step S8, where the correction instruction portion 12c supplies a correction instruction signal to the brightness correcting mechanism 2 or the like to correct the sensitivity, and then the correction is ended (step S9).

If the decision at step S4 is that the correction can be made by a software correction, control goes to step S10, where a rough correction portion 12d corrects the coordinates over the whole standard sample (rough corrections).

Then, control goes to step S11, where the rough correction portion 12d calculates the amount of the coordinate deviation and makes a decision as to whether or not the calculated amount of deviation is within a tolerable value. If the calculated amount of deviation is within the tolerable value, the rough correction portion 12d checks the sensitivity in step S12. If the amount is within the tolerable value, control passes to step S13, where the correction is ended.

If the checked sensitivity is outside the tolerance in step S12, the rough correction portion 12d corrects the sensitivity in step S14.

If the calculated amount of coordinate deviation is outside the tolerance in step S11, control goes to step S15, where a fine correction portion 12e corrects the coordinates in each region obtained by dividing the standard sample 6h.

In step S16, the sensitivity is checked. If the amount of coordinate deviation is within the tolerable value, the correction is ended in step S17.

If the amount of sensitivity deviation is outside the tolerable value in step S16, the sensitivity is corrected in step S18, and the correction is terminated (step S19).

As described previously, in embodiment 1 of the present invention, the coordinates of the detected defect can be detected by inspecting the standard sample 6h on which the artificial defects 16 are disposed.

Since the artificial defects 16 on the standard sample 6h have a known size (brightness) and are located in known positions, it follows that stage position information, conveyance error, beam position on the sample, and detected brightness information can be obtained by detecting the standard sample 6h.

A correction either of an in-plane distribution across the inspected object or of brightnesses (sizes) can be made, as well as a correction of the detection position, by providing feedback control of the correction mechanism portions including the sample transport portion 13 and the stage portion 7 based on these types of information so as to correct the coordinate positions.

Figure 9:
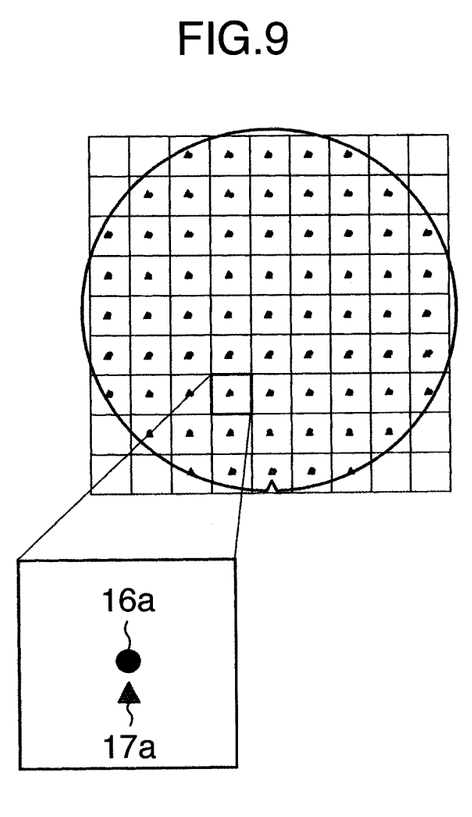
FIG. 9 is an explanatory view illustrating the manner in which the magnitude of an inspection result can be corrected by making a brightness correction in embodiment 1 of the invention.

For example, as shown in FIG. 9, in a case where the size of each artificial defect 16a is 50 nm and the size of a detected defect 17a, i.e., inspection result, is 46 nm, the detected defect 17a, i.e., the detection result, can be corrected to 50 nm by making a correction to the detection result or enhancing the brightness by the brightness correction mechanism. The sensitivity decrease due to an aging variation of the instrument can be corrected for each inspection of the standard sample. Stable state of operation of the instrument can be maintained at all times.

Figure 10:
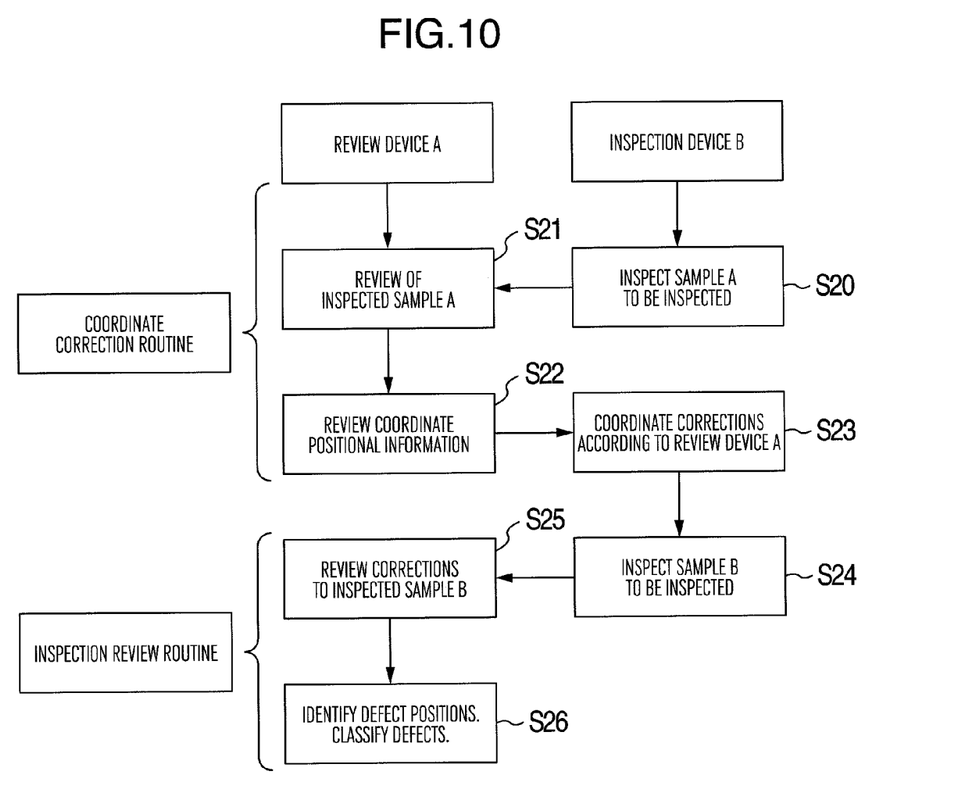
FIG. 10 is a flowchart schematically illustrating the whole operation of a comparative example that is an example different from the invention.

FIG. 10 is a flowchart of the whole operation of an example of a case in which corrections are made and defects are confirmed without using any standard sample, unlike the present invention, and is a chart showing one example for comparison with the present invention.

Figure 11:
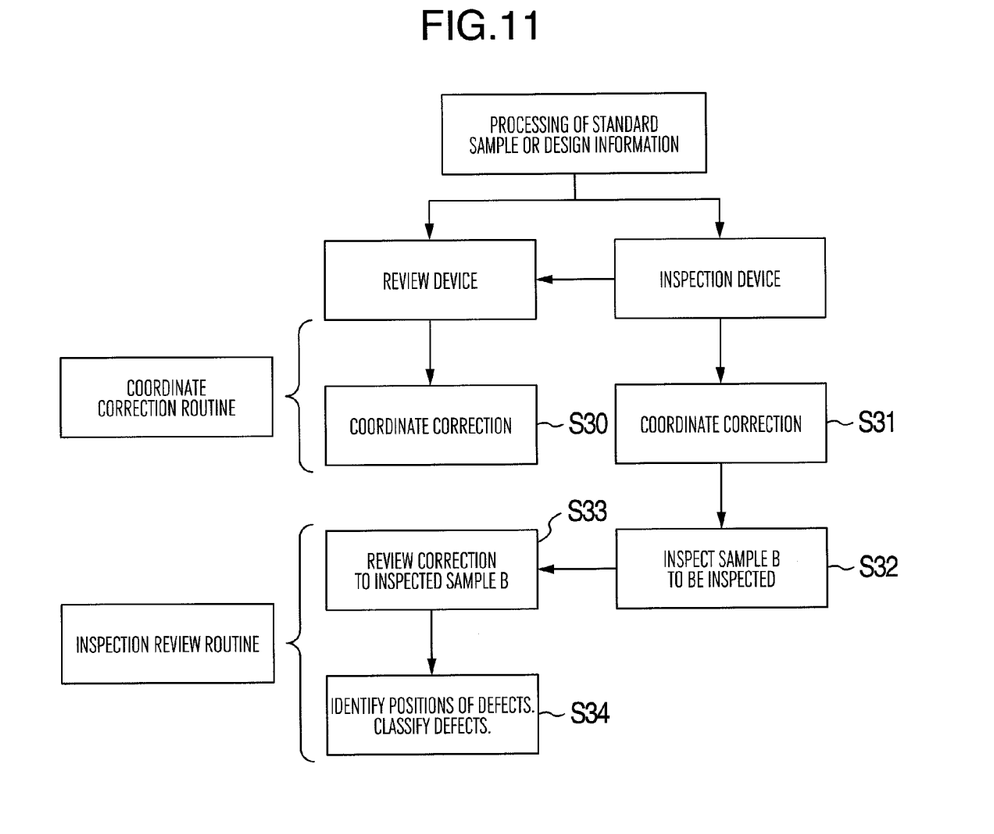
FIG. 11 is a flowchart schematically illustrating the whole operation in the present invention.

FIG. 11 is a flowchart of the whole operation in a case where corrections are made and defects are confirmed using a standard sample in accordance with an embodiment of the present invention.

In FIG. 10, a sample A to be inspected is inspected by an inspection device B (step S20). The inspected sample A is reviewed with a review device A (step S21).

And, coordinate position information about the inspected sample A is obtained by the review device A (step S22).

Subsequently, coordinate corrections are made by the inspection device B according to the coordinate position information derived by the review device A (step S23).

Then, the inspection device B inspects the inspected sample B using the corrected coordinates (step S24). The review device A makes a review correction of the inspected sample B (step S25). The positions of defects are identified and the defects are classified (step S26).

In the example shown in FIG. 10, coordinate position information about the inspected sample A is obtained by the review device A, and the coordinates of the inspection device B are corrected according to the information. Accordingly, the sample inspected by the inspection device B must be reviewed by the review device A. Where other review device is used, it is necessary that a sample inspected by the inspection device B be newly reviewed and that coordinate position information be obtained.

In contrast, in the case of the present invention shown in FIG. 11, coordinate corrections are made while both inspection device and review device use a standard sample. Therefore, defects can be inspected with no restrictions on the inspection device or on the review device.

That is, in FIG. 11, coordinate corrections are made to the standard sample on which a defect is formed, by the use of a review device and an inspection device (steps S30 and S31). Consequently, the review device and the inspection device share common coordinates.

The inspection device inspects the inspected sample B (step S32). The review device makes a review correction to the inspected sample B (step S33), identifies the positions of defects, and classifies the defects (step S34).

FIB processing or stepper photolithography is used for the standard sample used in the present invention, and defects are formed. With these methods of processing, it is easy to obtain information about the positions at which artificial defects are processed, as well as design information.

In the example shown in FIG. 10, it is necessary to make coordinate corrections while moving the inspected sample A to and fro between the inspection device and the review device. Hence, a long time is also required to make coordinate corrections.

In the present invention, if each of the inspection device and the review device makes coordinate corrections based on processing information or design information through the use of processing information and design information about the standard sample, a line can be built in which any review device can observe defects with equal performance without identifying the review device relative to the inspection device.

Because the coordinate accuracy is improved, defects closely spaced from each other can be separated. It is easy to grasp the shapes of defects. When defect kinds are classified, the classification accuracy is improved.

Defects can be separated from each other. Variations in the number of detected defects are suppressed. Variations among individual machines can be reduced.

Because conveyance errors and optical axis deviation in a defect detection device can be corrected, the stability of the instrument can be improved. Management of the state of the instrument can be facilitated. Stable state of the inspection device can be accomplished.

Since the coordinate accuracy in the defect detection device is improved, the observation time of the defect review device is reduced. Also, the observation accuracy is improved. Therefore, an improvement in the yield in semiconductor manufacturing steps can be accomplished.

Processing position information about a standard sample and design values are previously available by using an inspected object having artificial defects disposed at known positions over the whole surface of the object as a wafer for calibration of standard coordinates. Therefore, no corrections are necessary after the inspection device and the review device perform an inspection and a review, respectively. This leads to a great decrease in time.

Furthermore, coordinate errors in plural instruments can be eliminated. A line can be built in which observations can be made with no restrictions on the review device.

Figure 12:
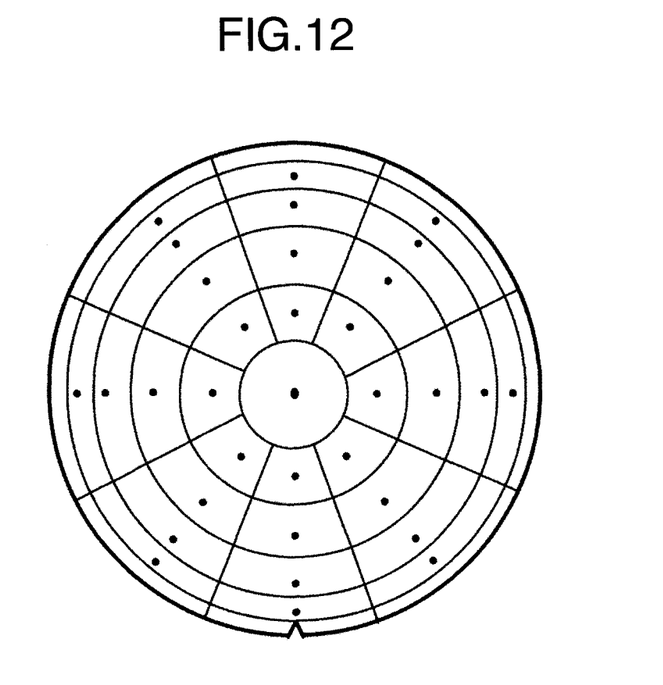
FIG. 12 is a view showing another method of dividing a standard sample.

Additionally, the example shown in FIG. 2 shows an example in which the standard sample 6h is divided into plural squares of the same area. As shown in FIG. 12, the sample may be divided into plural concentric circles which in turn are divided by plural lines extending radially. Further, the sample may be divided into plural squares, and the square corresponding to the central portion of the standard sample 6h may have a larger area, while surrounding squares may have a smaller area.

Although the foregoing description has been provided regarding the embodiment, the present invention is not restricted thereto. It is obvious to those skilled in the art that various changes and modifications are made within the spirit of the present invention and the scope of the accompanying drawings.

Reference Signs List
1: light source
2: brightness correcting mechanism
3: optical axis correcting mechanism
4a-4c: mirrors
5a, 5b, 8: condenser lenses
6: sample
6h: standard sample
7: XZ seater stage
9: detector
10: amplifier
11: foreign material/defect decision mechanism
12: data processing and controlling portion
12a: coordinate deviation amount calculating portion
12b: correction method determining portion
12c: correction instruction portion
12d: rough correction portion
12e: fine correction portion
13: sample transport portion
16: artificial defects
17: detected defect
20: FIB instrument

The invention claimed is:

1. A method of inspecting surface defects by illuminating an inspected object with illuminating light, detecting scattering light from the inspected object, and inspecting detects on a surface of the inspected object, said method comprising the steps of:
   forming defects having known coordinates on a standard sample;
   illuminating the standard sample with the illuminating light and detecting scattering light from the standard sample;
   correcting image coordinates of detected defects on the surface of the standard sample based on the known coordinates; and
   detecting at least one defect on the surface of the inspected object based on the corrected image coordinates,
   wherein the differences between image coordinates of the detected defects on the surface of the standard sample and the known coordinates are calculated, a decision is made as to whether each coordinate difference is greater than a given value, and in a case where the coordinate difference is greater than the given value, a mechanism of detecting the scattering light is adjusted and in a case where the coordinate difference is equal to or less than the given value, the image coordinates of the detected defects are corrected based on the coordinate difference and the defects on the surface of the inspected object are inspected based on the corrected image coordinates.

2. The method of inspecting surface defects of claim 1, wherein in a case where said coordinate difference is less than the given value, all of the coordinates of the obtained image coordinates are corrected based on the coordinates of the standard sample, total differences between all corrected coordinates and the coordinates of the standard sample are calculated, the standard sample is divided into plural regions if the calculated total differences are outside a tolerance, a region difference between the standard sample and the obtained image coordinate is calculated for each region obtained by the division, image coordinates are corrected for each region obtained by the division, and defects on the surface of the inspected object are inspected based on the corrected image coordinates.

3. The method of inspecting surface defects of claim 2, wherein said coordinate difference is an amount of deviation in a rotational direction, an amount of elongating or shrinking deviation, an amount of deviation of transport, or an amount of deviation of an optical axis.

4. The method of inspecting surface defects of claim 2, wherein at least one defect is formed on each of the plural regions formed by dividing the standard sample.

5. The method of inspecting surface defects of claim 2, wherein for each of the regions obtained by the division, image coordinates are corrected and then a decision is made as to whether a defect sensitivity is outside a tolerance, and wherein if the sensitivity is outside the tolerance, a correction is made such that the defect detection sensitivity is brought to within the tolerance.

6. A surface-defect inspection device comprising:
   a light source;

a movable stage on which an object to be inspected is disposed;

illumination unit which directs light from the light source at the inspected object disposed on the stage;

scattering light detection unit which detects scattering light from the inspected object;

defect detection unit which detects at least one defect on a surface of the object based on the scattering light detected by the scattering light detection unit; and a data processing and controlling portion which controls operation of the stage and of the illumination unit, illuminating a standard sample on which defects of known coordinates have been previously formed with illuminating light, detecting scattering light from the standard sample, and correcting image coordinates of the detected defects on the surface of the standard sample based on the known coordinates, wherein said data processing and controlling portion calculates the differences between the image coordinates of detected defects on the surface of said standard sample and the known coordinates, makes a decision as to whether each coordinate difference is greater than a given value, adjusts said scattering light detection unit if the coordinate difference is greater than the given value, and corrects obtained image coordinates based on the coordinate difference and inspects the defects on the surface of the inspected object based on the corrected image coordinates if the coordinate difference is less than the given value.

7. The surface-defect inspection device of claim 6, wherein in a case where said coordinate difference is less than the given value, said data processing and controlling portion corrects all of the obtained image coordinates based on the coordinates of the standard sample and calculates total differences between all corrected coordinates and the coordinates of the standard sample, and wherein in a case where the calculated total differences are outside a tolerance, the data processing and controlling portion divides the standard sample into plural regions, calculates a region difference between the standard sample and the obtained image coordinate for each region obtained by the division, corrects the image coordinate for each region obtained by the division, and inspects defects on the surface of the inspected object based on the corrected image coordinate.

8. The surface-defect inspection device of claim 7, wherein said coordinate difference is an amount of deviation in a rotational direction, an amount of elongating or shrinking deviation, an amount of deviation of transport, or an amount of deviation of an optical axis.

9. The surface-defect inspection device of claim 7, wherein at least one defect is formed on each of the plural regions formed by dividing the standard sample.

10. The surface-defect inspection device of claim 7, wherein for each of the regions obtained by the division, image coordinates are corrected and then a decision is made as to whether a defect sensitivity is outside a tolerance, and wherein if the sensitivity is outside the tolerance, a correction is made such that the defect detection sensitivity is brought to within the tolerance.

* * * * *